United States Patent
Morgan

(10) Patent No.: US 6,426,201 B1
(45) Date of Patent: Jul. 30, 2002

(54) β-GLUCAN PRODUCTS AND EXTRACTION PROCESSES FROM CEREALS

(75) Inventor: Keith Raymond Morgan, Petone (NZ)

(73) Assignee: Gracelinc Limited, Lower Hutt (NZ)

( * ) Notice: Subject to any disclaimer, the term of this patent is extended or adjusted under 35 U.S.C. 154(b) by 0 days.

(21) Appl. No.: 09/147,991

(22) PCT Filed: Sep. 25, 1997

(86) PCT No.: PCT/NZ97/00119

§ 371 (c)(1),
(2), (4) Date: May 20, 1999

(87) PCT Pub. No.: WO98/13056

PCT Pub. Date: Apr. 2, 1998

(30) Foreign Application Priority Data

Sep. 25, 1996 (NZ) .................................. 299441
Jun. 10, 1997 (NZ) .................................. 328049

(51) Int. Cl.$^7$ ..................... C12P 19/14; A61K 31/715
(52) U.S. Cl. ..................... 435/99; 435/101; 435/93; 435/72; 426/28; 536/123.12; 536/123.1; 536/128; 514/54
(58) Field of Search ..................... 435/99, 101, 93, 435/72; 426/28; 536/123.12, 123.1, 128; 514/54

(56) References Cited

U.S. PATENT DOCUMENTS

| | | | |
|---|---|---|---|
| 4,028,468 A | | 6/1977 | Hohner et al. |
| 4,110,163 A | * | 8/1978 | Hjortshoj et al. ............ 435/200 |
| 4,428,967 A | * | 1/1984 | Goering et al. ............... 426/28 |
| 4,871,571 A | | 10/1989 | Jensen et al. |
| 4,960,697 A | | 10/1990 | Johal et al. |
| 4,996,063 A | | 2/1991 | Inglett |
| 5,013,561 A | | 5/1991 | Goering et al. |
| 5,063,078 A | | 11/1991 | Foehse |
| 5,082,673 A | | 1/1992 | Inglett |
| 5,106,640 A | | 4/1992 | Lehtomaki et al. |
| 5,155,032 A | * | 10/1992 | Tanaka et al. .............. 435/184 |
| 5,458,893 A | | 10/1995 | Smith |
| 5,512,287 A | | 4/1996 | Wang et al. |
| 5,614,242 A | | 3/1997 | Fox |
| 5,686,123 A | | 11/1997 | Lindahl et al. |

FOREIGN PATENT DOCUMENTS

WO    WO 95/23514    * 8/1995

OTHER PUBLICATIONS

Meredith et al, Canadian J. Chem. 31:653–664, 1953.*
Böhm, N. et al., "Rheological studies of barley (1→3)(1→4)-β-glucan in concentrated solution: investigation of the viscoelastic flow behaviour in the sol–state", *Carbohydrate Research*, vol. 315, pp. 293–301 (1999).
Peter J. Wood, et al.; "Large–Scale Preparation and Properties of Oat Fractions Enriched in (1→3)(1→4)–β–D–Glucan"; *Cereal Chemistry*; 1989, vol. 66, No. 2, pp. 97–103.
Jean–Louis Doublier, et al.; "Rheological Properties of Aqueous Solutions of (1→3)(1→4)–β–D–Glucan from Oats(Avena sativs L.)"; *Rheology*; 1995; vol. 72, No. 4, pp. 335–340.
X.S. Yin, et al.; "An Approach to the Identification of a ) β–Glucan Solubilase from Barley"; *J. Inst. Brew.*; 1988; vol. 95, pp. 327–330.
X.S. Yin, et al.; "Substrate Specificity and Nature of Action of Barley β–Glucan Solubilase"; *J. Inst. Brew.*; 1989, vol. 95, pp. 105–109.
X.S. Yin, et al.; "Field Fungi and β–Glucan Solubilase in Barley Kernels"; *J. Inst. Brew.*; 1989; vol. 95, pp. 195–198.
H. Igarashi, et al.; "Chemical Structure of the β–Glucan Isolated from the Precipitates"; *J. Inst. Brew.*; 1969; vol. 75, pp. 292–299.

* cited by examiner

*Primary Examiner*—Francisco Prats
(74) *Attorney, Agent, or Firm*—Merchant & Gould P.C.

(57) ABSTRACT

A process for obtaining β-glucan from cereal by extracting with water and without deactivation of enzymes associated with the cereal. A process for controlling the average molecular weight of β-glucan extracted from cereal by controlling the extraction time. A process for recovering β-glucan from an aqueous solution of β-glucan comprising freezing the solution, allowing the solution to thaw and separating solids from the resultant suspension. A β-glucan produced by any of these processes. A β-glucan which forms a gel when a heated solution of the β-glucan cools. The use of β-glucan in treating various health disorders, as an additive in cosmetics and foods, and as a film forming agent. A cereal from which β-glucan has been extracted for use as animal feed or in brewing processes.

30 Claims, No Drawings

β-GLUCAN PRODUCTS AND EXTRACTION PROCESSES FROM CEREALS

FIELD OF INVENTION

This invention relates to novel substances which can be extracted from cereals, novel extraction procedures, and the use of the products as therapeutic agents, biocompatible films and as additives in food and cosmetics.

BACKGROUND

β-Glucan polysaccharides present in cereals comprise D-glycopyranosyl units. The units are linked together by (1→3) or (1→4) β-linkages. β-Glucans of this type comprise up to approximately 15% of the solids in oats and barley cereals. They typically have a molecular weight of around 2.5 million.

β-Glucans are useful as soluble dietary fibre. Soluble fibre remains undigested except by colonic microflora in the lower intestines. This enhances the growth of bacteria beneficial to health. Soluble dietary fibre is believed to have a role in the prevention of certain diseases including colonic cancer and diseases associated with high serum cholesterol levels. Soluble fibre can be used for the treatment and prevention of constipation, for the improvement of bowel regularity, and for the regulation of the glycaemic response associated with the digestion of many substances.

β-Glucans are considered to have hypocholesterolemic activity. β-Glucans are also useful as food ingredients. They have neutral flavours and provide bulk in addition to having desirable mouthfeel and texture characteristics. In this context, β-glucans are known as fat replacements in some foods.

The reported methods of extracting β-glucans from cereal involve a number of steps. First, the milled cereal is treated to deactivate enzymes associated with the cereal. Then the β-glucan is extracted from the cereal into warm water after which the solids are removed from the solution.

Large quantities of water-miscible organic solvents are added to the solution to precipitate the β-glucan, generally along with other polysaccharides. The β-glucan is of low purity and of generally high molecular weight. It is also known to carry out the enzyme deactivation step after the water extraction rather than as a first step. The deactivation step inhibits hydrolysis of the β-glucan thereby maintaining a high average molecular weight of the β-glucan.

Aqueous solutions of the β-glucan obtained via the known methods have minimal functionality with respect to temperature. They are generally high molecular weight gums and form viscous aqueous solutions although they do not dissolve in water easily.

The β-glucans obtained by the reported methods can contain arabinoxylans and starch. These impurities can be responsible for the formation of viscous aqueous solutions during extraction which are difficult to process. Gummy or tacky solids can result when the solids are recovered as a dry product. These products are difficult to redissolve, even at high temperatures.

The known methods of recovering β-glucan from the aqueous solution include precipitation of the β-glucan by the addition of a water miscible organic solvent (such as ethanol) followed by filtration, and spray- or freeze-drying of the precipitate.

The extraction procedures suggested by the prior art have limited commercial potential in view of the number of steps and hence the cost involved.

SUMMARY OF INVENTION

It is an object of this invention to provide a β-glucan product and a simple and effective method of extracting β-glucan, or to at least provide the public with a useful alternative.

In a first aspect of this invention there is provided a process for obtaining β-glucan, having a lower average molecular weight than in its native state, from cereal comprising:

mixing the cereal with water to form a slurry of an aqueous solution of β-glucan and a solid residue such that the β-glucan is partially hydrolysed by one or more enzymes associated with the cereal to give β-glucan having a lower average molecular weight than in its native state, separating the aqueous solution from the solid residue, and recovering the β-glucan from the aqueous solution, wherein there is there is no step of deactivation of the one or more enzymes during the process.

In accordance with a second aspect of this invention there is provided a process for recovering β-glucan from an aqueous solution of β-glucan comprising:

freezing the solution, thawing the solution to give a precipitate in water, and separating the precipitate from the water, wherein the major non-aqueous component of the precipitate is β-glucan.

The invention provides a β-glucan produced by any of the processes of the first and second aspects of the invention.

The invention also provides a β-glucan extracted from cereal which forms a gel when dissolved in heated water and then allowed to cool.

In accordance with a further feature of the invention there is provided a composition containing β-glucan for use as a hypocholesterolemic agent. A composition containing β-glucan is also provided for use in treating or preventing constipation, for regulating bowel activity, or for regulating glycaemic response.

The invention also provides a method of treating hypercholesterolemia in a patient in need comprising administering to the patient an effective amount of β-glucan.

The invention further provides a method of treating or preventing constipation, a method of regulating bowel activity and a method of regulating glycaemic response, each method comprising administering to a patient in need an effective amount of β-glucan.

The invention provides the use of a β-glucan as a food ingredient, as an additive in cosmetic compositions, as a film forming agent in wound dressings and in food coatings, as a matrix for the slow release of an agent carried in the matrix, and for the modification of the properties of other polysaccharides.

The invention also provides an animal feed consisting of cereal from which β-glucan has been extracted to a substantial extent. The invention further provides a cereal for use in brewing processes wherein β-glucan has been extracted from the cereal.

DETAILED DESCRIPTION

The cereal used in this invention may be any β-glucan containing grain or plant material including, but not limited to, barley, oats, rice, rye, triticale, maize and wheat. The preferred cereal is barley. In addition, waxy cereals have the advantage over non-waxy cereals that less leeching of amylose from the starch granules into the extraction solution occurs.

The physical properties of β-glucans depend largely on their average molecular weight. The expression "high molecular weight β-glucan" as used herein means β-glucan having an average molecular weight substantially similar to the average molecular weight of β-glucan found in the cereal (typically $2 \times 10^6$ to $3 \times 10^6$). The expression "low molecular weight β-glucan" as used herein means β-glucan having a lower average molecular weight ($5 \times 10^3$ to $1.5 \times 10^6$) relative to the average molecular weight of β-glucan found in the cereal.

The average molecular weight of the β-glucan extracted from the cereal is a function of the amount of time the β-glucan is in contact with one or mole hydrolase enzymes associated with the cereal. Thus, when the cereal is mixed with water, the one or more hydrolase enzymes are believed to become activated with respect to reaction with the β-glucan. A portion of the β-glucan molecules are hydrolysed to smaller units leading to β-glucan recovered from the extraction process having low molecular weight.

The hydrolase enzymes associated with the cereal include enzymes endogenous to the cereal and also enzymes present in, or produced by, microorganisms which may have adhered to the cereal.

The average molecular weight of β-glucan obtained by aqueous extraction of cereal, without deactivation of hydrolase enzymes, can be controlled by controlling the time of the extraction. In the process of the first aspect of the invention cereal is mixed with water to form a slurry so that β-glucan is extracted from the cereal into solution. The longer the extraction time, the greater the amount of hydrolysis of the β-glucan. Therefore, a low molecular weight β-glucan can be obtained if no deactivation of the enzymes occurs. Additionally, β-glucan of predetermined average molecular weight can be obtained by predetermining the extraction time.

The cereal may be extracted with water at any temperature in the range 0–80° C., preferably 30–70° C., or more preferably 45–60° C. At temperatures above approximately 80° C., the enzymes associated with the cereal are thought to become deactivated.

It will be appreciated that the yield of β-glucan recovered from the cereal varies with water temperature during the extraction process. A higher temperature generally gives a higher yield.

The cereal may be mixed with water adjusted to a pH in the range 1–10, preferably 5–8.

In addition to controlling the average molecular weight of the β-glucan by controlling the extraction time, the partial hydrolysis of the β-glucan is anticipated to be assisted by the addition of exogenous β-glucan hydrolysing enzymes to the mixture or by the addition of acid of the mixture.

It is also anticipated that treatment of the aqueous mixture with an arabinoxylan degrading enzyme, such as xylanase, or a starch degrading enzyme, such as an amylase, will lead to a β-glucan product of improved purity.

Cooling the aqueous solution of β-glucan to a temperature between approximately 0° C. and 10° C. may lead to formation of a gel.

Any of the known processes for recovering β-glucan from an aqueous solution or the process of the second aspect of this invention may be employed to recover the low molecular weight β-glucan.

The cereal, which may be in the form of whole grain, bran, pollard, flour or other powder milled to a desired particulate size, may be stirred with water at approximately 50° C. until a desired amount of β-glucan is extracted into solution, for example, up to 48 hours, preferably up to 10 hours, more preferably up to 3 hours. The aqueous phase may then be separated from any remaining solid matter by centrifugation followed by decanting or filtration. The β-glucan present in the aqueous solution is then recovered preferably by the process of the second aspect of this invention.

The average molecular weight of the low molecular weight β-glucan recovered may be in the range up to 1,500,000, preferably up to 600,000, more preferably up to 300,000, for example, 5,000 to 50,000. It will be appreciated that the average molecular weight of the β-glucan recovered may vary from cereal to cereal and may vary depending on the form of the cereal. Hence, some experimentation may be required in order to predetermine the average molecular weight of the product for a given mixing time.

The process of the second aspect of the invention relates to the recovery of β-glucan from an aqueous solution of β-glucan by freeze-thawing the solution.

In this process, the aqueous solution can be formed by the process of the first aspect of this invention or by any of the known methods which result in a low molecular weight β-glucan product. The known methods generally require deactivation of the enzymes present in the cereal prior to the aqueous extraction of β-glucan. The β-glucan is then partially hydrolysed enzymatically or by treatment with acid to give low molecular weight β-glucan.

The aqueous solution is frozen at a temperature below 0° C., preferably at a temperature between approximately −20° C. and −10° C. It does not appear to be important how long the solution is kept frozen. The frozen solution is then allowed to thaw, preferably by standing at room temperature (15–25° C.).

The β-glucan product is recovered as a whitish solid particulate, gelatinous or stringy material which has precipitated out of solution. This is separated by filtration or other means from the aqueous phase and is essentially insoluble in cold water. The β-glucan product is then dried. Drying can be assisted by freezing the precipitate and then allowing it to thaw. This process removes further water from the solid material.

The precipitate may be dried by any known means including air drying, pressing, washing with an alcohol, heating or freeze drying.

The resultant β-glucan product has been found to be of high purity, generally 70% by weight of the total solids or greater. Redissolving the β-glucan containing product in water followed by repeating the freezing and thawing steps, provides a β-glucan product of higher purity for example, greater than 90%.

While the process provides a β-glucan product of high purity, it is anticipated that the use of an arabinoxylan degrading enzyme, such as a xylanase, and/or a starch degrading enzyme, such as an amylase, will improve the purity of the β-glucan by making it easier to remove undesired arabinoxylans and starch as readily soluble oligosaccharides. The degrading enzyme may be used prior to the freezing and thawing steps of the β-glucan product recovered following the freezing and thawing steps, may be redissolved in water and treated with one or more such degrading enzymes.

The β-glucans so isolated have novel functional properties. Products obtained by known processes form viscous solutions that have little or no structure over a temperature range of 0 to 100° C. The β-glucan produced by the present invention forms free-flowing solutions that can develop considerable structure. Gels may form at temperatures below approximately 60° C. and concentrations above about 0.5% w/w, preferably above 1% w/w.

A viscous fluid is a fluid which shows resistance to flow. Mobile liquids like water have low viscosity but liquids which flow with difficulty, such as treacle, have high viscosity.

The term "gel" as used herein is defined as a partially coagulated solid in which a liquid is dispersed. Gels are generally semirigid but easily deformed. Gums are soluble in water to give viscous solutions but do not coagulate to form gels.

In a preferred embodiment of the invention, there is provided a β-glucan product which forms a soft gel at a concentration above about 0.5% w/w.

Preferably, the β-glucan product is dissolved when the water is heated to above approximately 60° C. A gel forms when the solution cools.

Generally, β-glucan of lower molecular weight forms gels rapidly. For example, a 30,000 molecular weight β-glucan may begin to solidify after approximately 15 minutes whereas a 400,000 molecular weight β-glucan may take approximately two hours to form a gel. Of these β-glucans, those of higher molecular weight typically form stiffer gels.

Another feature of the invention is the use of the low molecular weight β-glucan to modify the properties of other polysaccharides, for example, other high molecular weight β-glucans.

The β-glucan product of this invention may be used as an hypocholesterolemic agent. It is also useful for treating or preventing constipation and for the regulation of bowel activity. In addition, the β-glucan product may be used to regulate the glycaemic response, i.e. increased blood sugar levels, following the digestion of certain foods.

The therapeutic agents of the invention can be prepared in composition form to be taken as tablets, capsules, solutions, suspensions or other type of composition. These compositions can be formed by any known method.

The low molecular weight β-glucan of the invention can be utilised for purposes other than as an hypocholesterolemic agent. The unique functional properties will have a variety of uses particularly in processed food products. It is preferred in accordance with the invention to simply add the β-glucan to food products. Because the β-glucans are natural food components, it is believed the consumer resistance to modified or unnatural food additives will not be prevalent.

One quality of the low molecular weight β-glucans of the invention is that they have a good mouth feel. This makes them suitable as a fat mimetic in food products. Their ability to form films which are edible makes them potentially useful as food coatings, for example, glazings. The film forming properties of β-glucans also enable them to be useful as films for wound dressings. β-Glucans appear to inhibit the formation of ice crystals in frozen foods. They are therefore useful in frozen foods where a smooth mouthfeel is desired, for example, ice cream.

Additionally, the pores in the solid structure of the gelled or dried β-glucan product of this invention are anticipated to enable the β-glucans to be used as slow release agents for pharmaceuticals and for flavours, for example, in foods.

Cereals containing β-glucan are used as stock feed, particularly as poultry or pig feed. They will not be as effective as a nutrient in view of the anti-nutrient activity of the β-glucans. By extracting the β-glucans, the remaining solid material will have increased value as an animal feed. This will particularly be the case with barley.

The invention further provides an animal feed containing cereals from which the β-glucan has been removed by a process involving solubilising the β-glucans into an aqueous solution and removing the solid material as the animal feed. The solid material may also be used in brewing processes to reduce problems such as clogged fillers caused by the precipitation of β-glucans from solution during processing. Typically at least 30% of the β-glucan has been removed from the cereal. Preferably, at least 50% has been removed. More preferably, at least 80% of the β-glucan has been removed.

The following examples illustrate the invention but are not to be construed as limiting:

EXAMPLE 1

1 Kilogram of a barley finished pollard flour fraction was gently stirred with 5 liters of water at 55° C. for three hours. The solids were centrifuged off and the supernatant was frozen at −20° C. The solution was thawed and the β-glucan solids remaining in the thawed solution were filtered and dried. The yield of β-glucan product was 26 g. The product was characterised by $^{13}C$ solution NMR (Table 1).

TABLE 1

| Peak Frequency (ppm)* | Peak Height |
| --- | --- |
| 103.04 | 67 |
| 102.79 | 132 |
| 94.96 | 60 |
| 79.21 | 107 |
| 78.17 | 61 |
| 75.37 | 137 |
| 74.70 | 135 |
| 73.82 | 66 |
| 73.51 | 90 |
| 68.65 | 59 |
| 61.27 | 59 |
| 60.71 | 139 |

*The $^{13}C$ NMR spectrum of the β-glucan product was recorded in $D_2O$ at 70° C. Peak positions are referenced to DMSO in water ( = 39.47 ppm)

EXAMPLE 2

5 Grams of a barley finished pollard flour fraction containing 3.9% β-glucan was mixed with 25 ml of water at 55° C. The mixture was occasionally stirred. After 2 hours the solids were centrifuged off and the supernatant was frozen at −20° C. for 12 hours. The frozen solution was thawed at room temperatures and the precipitated β-glucan product was filtered and oven dried at 80° C. Total yield of β-glucan product was 0.18 g.

EXAMPLE 3

5 Grams of a barley bran flour fraction was mixed with 25 ml of water at 55° C. The mixtures was occasionally stirred. After 2 hours the solids were centrifuged off and the supernatant was frozen at −20° C. for 12 hours. The frozen solution was thawed at room temperature and the precipitated β-glucan product was filtered and oven dried at 80° C. Total yield of β-glucan product was 0.065 g.

EXAMPLE 4

5 Grams of a barley pollard flour fraction was mixed with 25 ml of water at 55° C. The mixture was occasionally stirred. After 2 hours the solids were centrifuged off and the supernatant was frozen at −20° C. for 12 hours. The frozen solution was thawed at room temperature and the precipitated β-glucan product was filtered and oven dried at 80° C. The solids remaining after centrifuging were subjected to another extraction procedure identical to the first extraction procedure. Total yield of recovered β-glucan product was 0.19 g.

EXAMPLE 5

5 Grams of a finished pollard barley flour fraction were heated with occasional stirring in 25 ml of distilled water at 55° C. for ½ hr. The solids were centrifuged off and the supernatant was frozen at −10° C. The frozen solution was thawed and the precipitated β-glucan product was filtered and dried. The yield of β-glucan product was about 0.16 g. The molecular weight of the product was examined using gel permission chromatography (GPC). The results suggest that the average molecular weight of this product was about 560,000.

EXAMPLE 6

140 Grams of a barley pollard flour fraction were heated at 50° C. in 700 ml of water with occasional stirring. After 0.5 hr the solids were removed by centrifuging. The recovered supernatant was then frozen at −10° C. After one day the frozen supernatant was allowed to thaw at room temperature. The thawed solution consisted of a gelatinous precipitate of β-glucan product which was removed by centrifugation. The gelatinous β-glucan product was washed and then frozen and thawed for a second time to give a more fibrous β-glucan product. This product could be further dehydrated by pressing out excess water, washing with ethanol and then drying in air. The yield of fibrous β-glucan product was about 3 g.

EXAMPLE 7

A very pure β-glucan product was prepared as follows: 100 g of barley pollard flour fraction was mixed with 500 ml of water at 55° C. After 2 hr the solids were centrifuged off and the supernatant was then frozen at −10° C. for one day. The frozen supernatant was thawed and the precipitated β-glucan product was removed by filtration. The recovered material was then redissolved in water at 80° C. The β-glucan solution was again frozen at −10° C. for one day and allowed to thaw. The β-glucan product was recovered from solution by filtration and was washed with water. The filtrate was then oven dried. Yield of β-glucan product was 3 g and a McCleary assay [1] indicated that the purity was 95%.

EXAMPLE 8

In a series of experiments a barley pollard fraction was extracted at different temperatures and for various times. Extraction temperatures were varied from ambient temperature (25° C.) to 55° C. and extraction times were varied from 0.5 hours to 5 hours. Molecular weights were determined by gel permeation chromatography (GPC). For each experiment β-glucan was extracted from 5 g of barley pollard into 25 ml of water for varying times and extraction temperatures. The solids were centrifuged off and the supernatant was then frozen at −10° C. for one day. The solution was then thawed at room temperature. The β-glucan that precipitated was filtered and dried. The yield was recorded and molecular weight profile was determined by GPC. Results are recorded in Table 2. Percentage yields given in Table 2 are based on total β-glucan content (6.8%) in the dry barley pollard [1]. The yield has been corrected for the amount of liquid remaining in the solids after centrifuging and by assuming the β-glucan content of the freeze/thaw precipitate is 80% (unless actually determined).

Generally it was found that the yield only depended on the temperature of the extraction process whereas the molecular weight at the GPC peak maximum was dependent only on the extraction time.

TABLE 2

| EXTRACTION TEMP(° C.) | EXTRACTION TIME (hr) | YIELD[1] (%) | β-GLUCAN CONTENT[2] (%) | MW AT PEAK MAXIMUM |
| --- | --- | --- | --- | --- |
| 25 | 0.5 | 32 | 83 | 62000 |
|  | 2 | 33 |  | 53000 |
|  | 3.5 | 34 |  | 45000 |
|  | 5 | 24 |  | 36000 |
| 35 | 5 | 29 |  | 29000 |
| 40 | 0.5 |  | 78 | 79000 |
| 45 | 2 | 47 |  | 49000 |
|  | 5 | 34 |  | 31000 |
| 55 | 0.5 | 48 | 84 | >100000 |
|  | 2.75 | 84 |  | 62000 |
|  | 5 | 68 |  | 35000 |

[1]Calculation based on total β-glucan content of the barley pollard.
[2]McCleary assay for β-glucan [1].
[1] McCleary, B. V. and Codd, R. (1991) Journal of the Science of Food and Agriculture, 55, 303–312.

EXAMPLE 9

5 Grams of a barley finished pollard flour was mixed with a 0.02 moles/liter of hydrochloric acid solution and the mixture left for 0.5 hr. The acid was then centrifuged off and the remaining flour washed with two portions of water. Any remaining water was centrifuged off. The wet flour was then mixed with 25 ml of water, and the water flour mixture was heated to 55° C. for 2 hours. The solids were centrifuged off and the supernatant was frozen at −10° C. for 12 hours. The frozen solution was then thawed and the gelatinous precipitate was collected and dried. Yield of β-glucan product was 0.07 g.

EXAMPLE 10

5 Grams of a barley finished pollard flour was mixed with 25 ml of water. The mixture was adjusted to pH=10 with sodium carbonate solution. The mixture was then heated to 45° C. for 2 hr. Solids were centrifuged off and supernatant was then frozen at −10° C. for 12 hours. The frozen solution was then thawed and the fibrous precipitate was collected and dried. Yield of β-glucan product was 0.15 g.

EXAMPLE 11

A high quality β-glucan product was produced by a seven step pilot plant extraction.

1. Extraction 78.9 kg of black barley pollard was mixed with 400.2 kg of tap water at 50° C. The barley/water slurry was held at 50 C. for 30 minutes.

2. Solids Removal

The slurry was then fed through an APV Scroll Decanter centrifuge at 2.96 kg/minute. 313.6 kg of supernatant was produced.

3. Clarification

The supernatant from the scroll decanter was fed through a Westfalia SAOH Disc Stack centrifuge at 1.9 kg/minute. 303.2 kg of supernatant was collected.

4. Freeze Thaw 1

The clarified supernatant was frozen and held at −18° C. for 2 days. The frozen supernatant was then allowed to thaw at room temperature for 3 days.

5. Concentration of Precipitated β-Glucan from Freeze Thaw 1

Supernatant was decanted using a peristaltic pump. 60 kg of precipitate slurry remained after decanting.

6. Clarification of Redissolved β-Glucan

The precipitate slurry was heated to 80° C. for 30 minutes to redissolve the precipitated β-glucan product. The solution was then passed through a Westfalia SAOH centrifuge at 80 C. to remove fines. 56.1 kg of clarified supernatant was obtained.

7. Freeze Thaw 2

The redissolved β-glucan was frozen at −18° C. for 2 days. The frozen β-glucan was thawed at room temperature for 3 days. The slurry of β-glucan product and supernatant from the second freeze thaw was then passed through a Sharples basket centrifuge at 1 liter per minute. The gelatinous β-glucan product was then freeze-dried to remove remaining moisture.

8. Yield

The yield of β-glucan product from the process was 1.64 kg.

EXAMPLE 12

A film was formed from the β-glucan product prepared in Example 6 as follows. 17 mg of the β-glucan product was dissolved in 0.5 ml of water at 80° C. to form a clear solution. A 2.5 cm round pool of the solution was then allowed to dry on a polyethylene template. The dried film of the glucan product was found to have good clarity and tensile strength.

EXAMPLE 13

A moisturising cream was prepared from the following ingredients and the β-glucan product prepared in Example 11.

| Ingredient | Quantity |
| --- | --- |
| Mixture A | |
| Wheat germ oil | 5 ml |
| Tween 65 | 1.5 g |
| Sorbitol stearate | 1.5 g |
| Cetyl alcohol | 1 g |
| Mixture B | |
| Polyethylene glycol | 5 ml |
| β-glucan | 0.75 g |
| Water | 35 ml |

Mixture B was heated to 70° C. until all the β-glucan product had dissolved. Mixture A was melted at 70° C. Mixture B together with 0.2 g of n-propyl-4-hydroxybenzoate was then rapidly stirred with Mixture A at 70° C. The formulation was then allowed to cool to give the moisturising cream.

EXAMPLE 14

An Italian-style dressing was prepared from the following ingredients and the β-glucan product prepared in Example 11.

| Ingredient | Quantity |
| --- | --- |
| Water | 60 ml |
| White wine vinegar | 40 ml |
| Sugar | 8 g |
| Salt | 2 g |
| Garlic | 2 g |
| Dried paprika | 1 g |
| Dried majoram | 0.2 g |
| Dried basil | 0.2 g |
| β-glucan product | 2 g |

The β-glucan product was dissolved in the water at a temperature of 80° C. All the ingredients were immediately combined and blended for 3 minutes in a food-processor fitted with a blade attachment. The mixture was then allowed to cool and gel at a temperature of 4° C. to give the dressing.

EXAMPLE 15

An ice-cream was prepared using the following ingredients and the β-glucan product prepared in Example 11.

| Ingredients | Quantity |
| --- | --- |
| Water | 80 ml |
| Thick cream | 20 ml |
| Sugar | 12 g |
| Non-fat milk powder | 15 g |
| Vanilla | 2 ml |
| β-glucan product | 5 g |

The β-glucan product was dissolved in the water at 80° C. and then immediately mixed with the other ingredients in a food processor fitted with a blade attachment. The mixture was processed for 5 minutes. The processed mixture was then frozen at a temperature of −15° C. to produce an ice-cream having little or no ice crystal formation.

EXAMPLE 16

An orange cake containing no added fat was prepared from the following ingredients and the β-glucan product prepared in Example 11.

| Ingredients | Quantity |
| --- | --- |
| Cake flour | 180 g |
| Eggs (size 7) | 2 |
| Sugar | 85 g |
| Freshly-squeezed orange juice | 25 ml |
| Water | 60 ml |
| Baking soda | 1 g |
| Tartaric acid | 1 g |
| β-glucan product | 5 g |

The orange juice and water were combined then heated to a temperature of 80° C. The β-glucan product was then dissolved in the water and orange mixture at a temperature of 80° C. The mixture was then set aside for approximately 20 minutes to cool and gel. The eggs and sugar were blended in a cake mixer for 5 minutes. The dry ingredients were combined and mixed with the egg and sugar blend. The gelled orange and water mix was then blended in to this mixture. The resultant batter was baked in an oven at 160° C. for 20 minutes.

Although the invention has been described by way of example of example, it should be appreciated that variations and modifications may be made thereto, without departing from the scope of the invention as defined in the claims. Furthermore, where known equivalents exist to specific features given herein, such equivalents are incorporated as if specifically set forth herein.

INDUSTRIAL APPLICABILITY

The β-glucan products of this invention have a variety of uses. They are useful as additives in foods and in cosmetics due to their gel forming characteristics. They can form films which means they are useful as biocompatible films, for example, edible films for foods and films for use in wound dressings. The β-glucan products also have applications as pharmaceuticals, in particular, as cholesterol reducing agents.

What is claimed is:

1. A process for obtaining β-glucan, having a lower average molecular weight than in its native state, from cereal comprising:
   mixing the cereal with water to form a slurry of an aqueous solution of β-glucan and a solid residue such that the β-glucan is partially hydrolysed by one or more enzymes present with the cereal prior to mixing to give a β-glucan having a lower average molecular weight than in its native state,
   separating the aqueous solution from the solid residue,
   cooling the aqueous solution to a temperature below 10° C. so that a β-glucan gel forms; and
   recovering the β-glucan from the aqueous solution, wherein the process excludes any positive step of deactivation of the one or more enzymes.

2. A process as claimed in claim 1 wherein the cereal is in the form of a flour or flour fraction.

3. A process as claimed in claim 1 wherein the cereal is mixed with water at a temperature in the range of approximately 0–80° C.

4. A process as claimed in claim 1 wherein the temperature is in the range of approximately 45–60° C.

5. A process as claimed in claim 1 wherein the cereal is mixed with water at a pH in the range of approximately 1–10.

6. A process as claimed in claim 1 further comprising the step of adding one or more enzymes to the slurry or to the aqueous solution obtained from the separation step to assist the partial hydrolysis of the β-glucan.

7. A process as claimed in claim 1 further comprising the step of adding acid to the slurry or to the aqueous solution obtained from the separation step to assist the partial hydrolysis of the β-glucan.

8. A process as claimed in claim 1 further comprising treating the slurry or the aqueous solution obtained from the separation step with an arabinoxylan-degrading enzyme or a starch-degrading enzyme so that the β-glucan obtained has reduced amounts of arabinoxylan or starch impurities.

9. A process as claimed in claim 8 wherein the arabinoxylan-degrading enzyme is xylanase.

10. A process as claimed in claim 8 wherein the starch-degrading enzyme is an amylase.

11. A process as claimed in claim 1 wherein the average molecular weight of the β-glucan is less than approximately $1.5 \times 10^6$.

12. A process as claimed in claim 1 wherein the average molecular weight of the β-glucan is less than approximately $6.0 \times 10^5$.

13. A process as claimed in claim 1 wherein the average molecular weight of the β-glucan is less than approximately $3.0 \times 10^5$.

14. A process as claimed in claim 1 wherein the average molecular weight of the β-glucan is in the range of approximately $5 \times 10^3$ to $5 \times 10^4$.

15. A process as claimed in claim 1 wherein aqueous solution is cooled to a temperature sufficient to freeze the solution, the solution is then thawed to give a precipitate in water, and the precipitate is separated from the water, wherein a non-aqueous component of the precipitate is β-glucan.

16. A process as claimed in claim 15 wherein the solution is frozen at a temperature between approximately −20° C. and 0° C.

17. A process as claimed in claim 15 wherein the solution is thawed at a temperature of approximately 15–25° C.

18. A process as claimed in claim 15 wherein the precipitate is separated from the water by filtration or centrifugation and is then dried.

19. A process as claimed in claim 15 further comprising redissolving in water the precipitate recovered from the water and repeating the freezing, thawing and separating steps.

20. A process as claimed in claim 19 wherein the precipitate is again frozen and then thawed to further remove water from the precipitate.

21. A process as claimed in claim 15 wherein the β-glucan is greater than approximately 30% by weight of the precipitate.

22. A process as claimed in claim 15 wherein the β-glucan is greater than approximately 70% by weight of the precipitate.

23. A process as claimed in claim 15 wherein the β-glucan is greater than approximately 90% by weight of the total precipitate.

24. A process as claimed in claim 15 wherein an arabinoxylan-degrading enzyme or a starch-degrading enzyme is added to the aqueous solution containing β-glucan prior to freezing the solution so that arabinxoylan or starch is degraded and the precipitate recovered from the suspension has a reduced amount of arabinoxylan or starch impurities.

25. A process as claimed in claim 15 wherein the solids recovered from the suspension are redissolved in water and treated with an arabinoxylan degrading enzyme or a starch degrading enzyme followed by repeating the freezing, thawing and separating steps to give a precipitate having reduced amounts of arabinoxylan or starch impurities.

26. A process as claimed in claim 25 wherein the arabinoxylan-degrading enzyme is xylanase.

27. A process as claimed in claim 24 wherein the starch-degrading enzyme is an amylase.

28. A process as claimed in claim 25 wherein the arabinoxylan-degrading enzyme is xylanase.

29. A process as claimed in claim 25 wherein the starch-degrading enzyme is an amylase.

30. A process as claimed in claim 1 wherein the cereal is barley, oats, rice, rye, triticale, maize or wheat.

* * * * *